US009732375B2

(12) United States Patent
Millar (10) Patent No.: US 9,732,375 B2
(45) Date of Patent: Aug. 15, 2017

(54) MOLECULAR DETECTION ASSAY USING DIRECT TREATMENT WITH A BISULPHITE REAGENT (75) Inventor: Douglas Spencer Millar, Revesby (AU)

(73) Assignee: HUMAN GENETIC SIGNATURES PTY. LTD., Randwick (AU)

( * ) Notice: Subject to any disclaimer, the term of this patent is extended or adjusted under 35 U.S.C. 154(b) by 648 days.

(21) Appl. No.: 14/342,093

(22) PCT Filed: Sep. 7, 2011

(86) PCT No.: PCT/AU2011/001156
§ 371 (c)(1),
(2), (4) Date: Jun. 16, 2014

(87) PCT Pub. No.: WO2013/033749
PCT Pub. Date: Mar. 14, 2013

(65) Prior Publication Data
US 2015/0086972 A1 Mar. 26, 2015

(51) Int. Cl.
C12Q 1/68 (2006.01)
C12Q 1/70 (2006.01)
(52) U.S. Cl.
CPC ........... *C12Q 1/6806* (2013.01); *C12Q 1/689* (2013.01); *C12Q 1/6886* (2013.01); *C12Q 1/6893* (2013.01); *C12Q 1/707* (2013.01); *C12Q 2600/158* (2013.01)
(58) Field of Classification Search
USPC ...................................... 435/6.11, 6.12, 91.2
See application file for complete search history.

(56) References Cited

U.S. PATENT DOCUMENTS

| 5,124,327 | A | 6/1992 | Greenlee et al. |
|---|---|---|---|
| 5,175,273 | A | 12/1992 | Bischofberger et al. |
| 5,414,077 | A | 5/1995 | Lin et al. |
| 5,418,149 | A | 5/1995 | Gelfand et al. |
| 5,629,156 | A | 5/1997 | Shah et al. |
| 5,656,744 | A | 8/1997 | Arnold et al. |
| 5,750,338 | A | 5/1998 | Collins et al. |
| 5,786,146 | A | 7/1998 | Herman et al. |
| 5,824,517 | A | 10/1998 | Cleuziat et al. |
| 5,952,174 | A | 9/1999 | Nikiforov et al. |
| 6,156,501 | A | 12/2000 | McGall et al. |
| 6,251,637 | B1 | 6/2001 | Blusch |
| 6,265,171 | B1 | 7/2001 | Herman et al. |
| 6,331,393 | B1 | 12/2001 | Laird et al. |
| 6,420,106 | B1 | 7/2002 | Gyllensten et al. |
| 6,521,411 | B2 | 2/2003 | Hecker et al. |
| 6,692,918 | B2 | 2/2004 | Kurn |
| 6,960,436 | B2 | 11/2005 | Cottrell |
| 7,008,770 | B1 | 3/2006 | Berlin |
| 7,288,373 | B2 | 10/2007 | Millar et al. |
| 7,413,855 | B2 | 8/2008 | Bergmann et al. |
| 7,501,240 | B2 * | 3/2009 | Birkner .................. C07H 21/00 435/6.12 |
| 7,504,207 | B2 | 3/2009 | Bergquist et al. |
| 7,527,948 | B2 | 5/2009 | Hudson et al. |
| 7,799,525 | B2 | 9/2010 | Millar |
| 7,803,580 | B2 | 9/2010 | Millar |
| 7,833,942 | B2 | 11/2010 | Millar et al. |
| 7,846,693 | B2 | 12/2010 | Millar et al. |
| 8,137,937 | B2 | 3/2012 | Markert-Hahn |
| 8,168,777 | B2 | 5/2012 | Millar et al. |
| 8,343,738 | B2 | 1/2013 | Millar et al. |
| 8,431,347 | B2 | 4/2013 | Millar et al. |
| 8,598,088 | B2 | 12/2013 | Millar et al. |
| 8,685,675 | B2 | 4/2014 | Millar et al. |
| 2002/0086324 | A1 | 7/2002 | Laird et al. |
| 2002/0142397 | A1 | 10/2002 | Collas et al. |
| 2003/0073081 | A1 | 4/2003 | Mukai et al. |
| 2003/0082600 | A1 | 5/2003 | Olek et al. |
| 2003/0119025 | A1 | 6/2003 | Olek et al. |
| 2003/0143577 | A1 | 7/2003 | Hogrefe et al. |
| 2004/0067559 | A1 | 4/2004 | McCarthy et al. |
| 2004/0086944 | A1 | 5/2004 | Grigg et al. |
| 2004/0203004 | A1 | 10/2004 | Bernard et al. |
| 2004/0219539 | A1 | 11/2004 | Millar et al. |
| 2005/0019762 | A1 | 1/2005 | Olek |
| 2005/0059003 | A1 | 3/2005 | Enoki et al. |
| 2005/0118578 | A1 | 6/2005 | Mineno et al. |
| 2005/0136417 | A1 | 6/2005 | Cole et al. |

(Continued)

FOREIGN PATENT DOCUMENTS

DE 103 31 107 B3 12/2004
EP 1 130 113 9/2001

(Continued)

OTHER PUBLICATIONS

Liu et al., "Direct Bisulfite Conversion from Biological Samples for High Resolution Methylation Detection", 2009 Science and Technology Symposium Poster #209, 2009 Life Technologies, 1 page.
Liu et al., "Direct Bisulfite Conversion from Archived Tumor Samples for Methylation Detection", 101th AACR Poster #182, 2010 Life Technologies, 1 page.
Liu et al., "Direct Methylation Detection from Cancer Cells, Blood and Tissues: High Speed Conversion Followed by High-resolution Melting, Methylation Specific PCT and Sequencing", 59th ASHG Poster #909, 2009 Life Technologies, 1 page.
European Extended Search Report dated Dec. 23, 2014 in Application No. 11871849.3, filed Sep. 7, 2011.
Asseline et al. Synthesis and binding properties of oligonucleotides covalently linked to an acridine derivative: New study of the influence of the dye attachment site. Bioconjugate Chem., 7:369-379 (1996).
Badal V. et al: "CpG methylation of human papillomavirus type 16 DNA in cervical cancer cell lines and in clinical specimens: Genomic hypomethylation correlates with carcinogenic progression" J Virol., 77(11): 6227-6234(Jun. 1, 2003).
Badal et al. The human papillomavirus-18 genome is efficiently targeted by cellular DNA methylation, Virology 324(2): 483-492 (Jul. 1, 2004).

(Continued)

*Primary Examiner* — Kenneth Horlick
(74) *Attorney, Agent, or Firm* — Knobbe Martens Olson & Bear LLP (57) ABSTRACT

A molecular detection assay including treating a biological sample directly with a bisulphite agent under conditions that allow cell disruption and nucleic acid treatment; removing the bisulphite agent from the treated sample; and detecting a target nucleic acid in the treated sample.

16 Claims, 3 Drawing Sheets

(56) References Cited

U.S. PATENT DOCUMENTS

| | | |
|---|---|---|
| 2005/0196392 A1 | 9/2005 | Andersen |
| 2005/0196792 A1 | 9/2005 | Fodor et al. |
| 2005/0202490 A1 | 9/2005 | Makarov |
| 2006/0014144 A1 | 1/2006 | Christensen et al. |
| 2006/0051771 A1 | 3/2006 | Murphy et al. |
| 2006/0068406 A1 | 3/2006 | Affholter et al. |
| 2006/0094009 A1 | 5/2006 | Vaughan et al. |
| 2006/0166203 A1 | 7/2006 | Tooke |
| 2006/0286576 A1 | 12/2006 | Lofton-Day |
| 2007/0020633 A1 | 1/2007 | Millar et al. |
| 2007/0020639 A1 | 1/2007 | Shapero |
| 2007/0020653 A1 | 1/2007 | Holliger et al. |
| 2007/0026070 A1 | 2/2007 | Vonwiller et al. |
| 2007/0042365 A1 | 2/2007 | Millar et al. |
| 2007/0065824 A1 | 3/2007 | Gutig |
| 2007/0178457 A1 | 8/2007 | Millar |
| 2007/0178459 A1 | 8/2007 | Millar et al. |
| 2007/0190530 A1 | 8/2007 | Birkner et al. |
| 2007/0264653 A1 | 11/2007 | Berlin et al. |
| 2008/0050738 A1 | 2/2008 | Millar |
| 2009/0029346 A1 | 1/2009 | Millar et al. |
| 2009/0042732 A1 | 2/2009 | Millar et al. |
| 2009/0130657 A1 | 5/2009 | Millar |
| 2009/0263909 A1 | 10/2009 | Millar et al. |
| 2010/0041013 A1 | 2/2010 | Millar et al. |
| 2010/0092972 A1 | 4/2010 | Millar et al. |
| 2010/0121056 A1 | 5/2010 | Christensen et al. |
| 2010/0221785 A1 | 9/2010 | Millar et al. |
| 2010/0286379 A1 | 11/2010 | Millar et al. |
| 2010/0304386 A1 | 12/2010 | Millar |
| 2011/0003700 A1 | 1/2011 | Millar |
| 2011/0136098 A1 | 6/2011 | Millar et al. |
| 2012/0021461 A1 | 1/2012 | Millar et al. |

FOREIGN PATENT DOCUMENTS

| | | |
|---|---|---|
| EP | 1 319 718 | 6/2003 |
| EP | 1 443 052 | 8/2004 |
| EP | 1 801 213 A2 | 6/2007 |
| EP | 2 034 029 A1 | 3/2009 |
| WO | WO 95/01456 | 1/1995 |
| WO | WO 95/22623 | 8/1995 |
| WO | WO 97/41254 | 11/1997 |
| WO | WO 97/45559 | 12/1997 |
| WO | WO 98/20157 | 5/1998 |
| WO | WO 98/29108 | 7/1998 |
| WO | WO 99/09211 | 2/1999 |
| WO | WO 99/14226 | 3/1999 |
| WO | WO 99/49081 | 9/1999 |
| WO | WO 00/44934 | 8/2000 |
| WO | WO 00/50869 A2 | 8/2000 |
| WO | WO 01/09374 A2 | 2/2001 |
| WO | WO 01/38565 A2 | 5/2001 |
| WO | WO 01/42493 A2 | 6/2001 |
| WO | WO 01/76451 A2 | 10/2001 |
| WO | WO 02/36821 A2 | 5/2002 |
| WO | WO 02/38801 | 5/2002 |
| WO | WO 02/46452 | 6/2002 |
| WO | WO 02/072880 | 9/2002 |
| WO | WO 02/097065 | 12/2002 |
| WO | WO 03/008623 | 1/2003 |
| WO | WO 03/048732 | 6/2003 |
| WO | WO 03/051901 A2 | 6/2003 |
| WO | WO 03/052132 A2 | 6/2003 |
| WO | WO 03/052133 A2 | 6/2003 |
| WO | WO 03/052134 A2 | 6/2003 |
| WO | WO 2004/015139 | 2/2004 |
| WO | WO 2004/065625 | 8/2004 |
| WO | WO 2004/090166 | 10/2004 |
| WO | WO 2004/096825 | 11/2004 |
| WO | WO 2004/111266 | 12/2004 |
| WO | WO 2005/021778 | 3/2005 |
| WO | WO 2005/056790 | 6/2005 |
| WO | WO 2005/113760 | 12/2005 |
| WO | WO 2006/058393 | 6/2006 |
| WO | WO 2006/066353 | 6/2006 |
| WO | WO 2006/125267 | 11/2006 |
| WO | WO 2007/106802 A2 | 9/2007 |
| WO | WO 2008/109945 | 9/2008 |
| WO | WO 2008/135512 A2 | 11/2008 |
| WO | WO 2008/150998 | 12/2008 |
| WO | WO 2009/067743 | 6/2009 |
| WO | WO 2009/070843 | 6/2009 |
| WO | WO 2009/079703 | 7/2009 |
| WO | WO 2011/046518 A1 | 4/2011 |

OTHER PUBLICATIONS

Bakker, et al., Methyl-CpG Binding Domain Protein 2 Represses Transcription from Hypermethylated gamma-Class Glutathione *S-Transferase Gene Promoters in Hepatocellular Carcinoma Cells*, JBC, 277(25): 22573-22580, Jun. 2002.

Baleriola et al. Comparison of a novel HPV test with the Hybrid Capture II (hcII) and a reference PCR method shows high specificity and positive predictive value for 13 high-risk human papillomavirus infections J Clin Vir., 42(1): 22-26 (May 1, 2008).

Bessho et al., Blockage of polymerase-catalyzed DNA chain elongation by chemically modified cytosine residues in templates and the release of blockage for readthrough, Nucl Acids Res. (1992) 20(16): 4213-4220.

Bleczinski et al. Steroid-DNA interactions increasing stability, sequence-selectivity, DNA/RNA discrimination, and hypochromicity of oligonucleotide duplexes. J. Am. Chem. Soc. 121:10889-10894 (1999).

Burmeister et al. Synthesis of novel phosphoramidite derivatives bearing pyrenyl and dansyl groups. Tetrahedron Letters. 36(21):3667-3668 (1995).

Cameron et al. NEOPLASIA: CpG island methylation in primary acute leukemia is heterogeneous and suggests density as a critical factor for transcriptional silencing, Blood, 94(7): 2445-2451, Oct. 1999.

Christensen et al. Intercalating nucleic acids containing insertions of 1-O-(1-pyrenylmethyl) glycerol: stabilisation of dsDNA and discrimination of DNA over RNA. Nucleic Acids Research. 30(22):4918-4925 (2002).

Clark et al. Bisulphite genomic sequencing of methylated cytosines. Laboratory Methods for the Detection of Mutations and Polymorphisms in DNA. Graham R. Taylor, Ed. CRC Press, New York (1997) pp. 151-162.

Clark et al. High sensitivity mapping methylated cytosines. Nucleic Acids Research, 22(15): 2990-2997 (1994).

Cohen et al, Hypermethylation of CpG Island Loci of Multiple Tumor Suppressor Genes in Retinoblastoma, Experimental Eye Research, 86(2): 201-206 (2008).

Cottrell et al., A real-time PCR assay for DNA-methylation-specific blockers. Nucleic Acid Research, 32(1):e10 (8 pages). Jan. 13, 2004.

D'Abbadie, et al., "Molecular Breeding of Polymerases for Amplification of Ancient DNA," Nature Biotechnology, (Aug. 2007) 25:939-943.

De Mesmaeker et al. Amide backbone modifications for antisense oligonucleotides carrying potential intercalating substituents: Influence on the thermodynamic stability of the corresponding duplexes with RNA- and DNA-complements. Bioorganic & Medicinal Chemistry Letters. 7(14):1869-1874 (1997).

Dean et al. Comprehensive human genome amplification using multiple displacement amplification. PNAS, 99(8): 5261-5266 (2002).

Eads, et al. MethyLight: a high-throughput assay to measure DNA methylation. Nucleic Acids Research, 28(8): E32.1-E32.8. (2000).

Edamoto et al., Alterations of RB1, p53 and Wnt Pathways in Hepatocellular Carcinomas Associated with Hepatitis C, Hepatitis B and Alcoholic Liver Cirrhosis, Int J Cancer (2003) 106: 334-341.

Esteller, et al., Inactivation of Glutathione S-Transferase P1 Gene by Promoter Hypermethylation in Human Neoplasia, Cancer Research, 58: 4514-4518, Oct. 1998.

Feil et al. Methylation analysis on individual chromosomes: improved protocol for bisulphite genomic sequencing. Nucleic Acids Research 22(4): 695-696 (1994).

(56) References Cited

OTHER PUBLICATIONS

Feng et al. Detection of hypermethylated genes in women with and without cervical neoplasia. J Nat Cancer Inst. 97(4): 273-282 (Feb. 16, 2005).
Francois et al. Recognition of hairpin-containing single-stranded DNA by oligonucleotides containing internal acridine derivatives. Bioconjugate Chem. 10:439-446 (1999).
Frommer, et al. "A genomic sequencing protocol that yields a positive display of 5-methylcytosine residues in individual DNA strands," Proc. Natl. Acad. Sci. 89: 1827-1831 (1992).
Grigoriev, et al. A Triple Helix-forming Oligonucleotide-Intercalator Conjugate Acts as a Transcriptional Repressor via Inhibition of NFkB Binding to Interleukin-2 Receptor a-Regulatory Sequence. J Biol Chem., 267 (5): 3389-3395 (1992).
Grunau, et al. "Bisulfite genomic sequencing: systematic investigation of critical experimental parameters." Nucleic Acids Research, (2001) vol. 29, No. 13e65, pp. 1-7.
Gu et al. Depletion of Saccharomyces cerevisiae tRNAHis Guanylyltransferase Thglp leads to uncharged tRNAH is with additional m5C, Mol Cell Biol. 25(18): 8191-8201 (Sep. 2005).
Håkelien et al. Reprogramming fibroblasts to express T-cell functions using cell extracts. Nature Biotechnology, 20(5): 460-466 (2002).
Håkelien et al. Novel Approaches to Transdifferentiation. Cloning and Stem Cells. 4: 379-387 (2002).
Herman et al. Unit 10.6 Methylation-Specific PCR, Current Protocols in Human Genetics, Published Online: May 1, 2001, pp. 10.6.1-10.6.10, DOI: 10.1002/0471142905.hg1006s16, Copyright © 2003 by John Wiley and Sons, Inc: http://onlinelibrary.wiley.com/doi/10.1002/0471142905.hg1006s16/full.
Herman, et al. "Methylation-specific PCR: a novel PCR assay for methylation status of CpG islands." (1996) Proc. Natl. Acad. Sci. 93:9821-9826.
Hitchcock, T.M. et al, "Cleavage of deoxyoxadenosine-containing oligodeoxyribonucleotides by bacterial endonuclease V", Nucleic Acids Research, 2004, vol. 32, No. 13, pp. 4071-4080.
Hosono, et al. "Unbiased Whole-Genome Amplification Directly from Clinical Samples." Genome Research; 13:954-964 (2003).
International Human Genome Sequencing Consortium, "Initial sequencing and analysis of the human genome," Nature, 409(6822): 860-921 (2001).
Kalantari, et al. "Conserved methylation patterns of human papillomavirus type 16 DNA in asymptomatic infection and cervical neoplasia," Journal of Virology, vol. 78, No. 23, Dec. 2004, pp. 12762-12772.
Kim, et al. "DNA hypermethylation in gastric cancer" Alimentary Pharmacology & Therapeutics, vol. 20, No. Suppl. 1, Jul. 2004 (Jul. 2004), pp. 131-142.
Kinoshita, et al. "Methylation of the androgen receptor minimal promoter silences transcription in human prostate cancer." Cancer Research, 60(13): 3623-3630 (Jul. 1, 2000).
Kono. "Nuclear transfer and reprogramming." Reviews of Reproduction, vol. 2 No. 2, pp. 74-80 (May 1997).
Korshun et al. Reagent for introducing pyrene residues in oligonucleotides. Bioconjugate Chem., 3:559-562 (1992).
Kozak, et al.: "Influence of secondary structure on binding and migration of 40S ribosomal subunits," Cell, vol. 19, 1980, pp. 79-90.
Lee, et al. Cancer Epidemiology, Biomarkers, Prevention, vol. 6, pp. 443-450, Jun. 1997.
Longo, M.C. et al., Use of Uracil DNA Glycosylase to Control Carry-Over Contamination in Polymerase Chain Reactions, Gene, vol. 93, No. I, pp. 125-128, Sep. 1990.
Malyukova, et al. Methylation of the Putative Tumor Suppressor Gene RASSF1A in Primary Cervical Tumors, Mol Biol. 38(6): 857-86, Nov. 2004.
Mann et al. Synthesis and properties of an oligodeoxynucleotide modified with a pyrene derivative at the 5'-phosphate. Bioconjugate Chem., 3: 554-558 (1992).

Masuko et al. Fluorescence resonance energy transfer from pyrene to perylene labels for nucleic acid hybridization assays under homogeneous solution conditions. Nucleic Acids Research, 28(8):e34, 8 pages (2000).
Melki, et al. Concurrent DNA Hypermethylation of Multiple Genes in Acute Myeloid Leukemia, Cancer Research, 59: 3730-3740, Aug. 1999.
Millar, et al. Detailed methylation analysis of the glutathione S-transferase pi (GSTPI) gene in prostate cancer, Oncogene 18(6): 1313-1324 (1999).
Millar, et al. A distinct sequence (ATAAA)n separates methylated and unmethylated domains at the 5'-end of the GSTPI CpG island. J. Biol. Chem., 275(32): 24893-24899 (2000).
Monk. Epigentic programming of differential gene expression in development and evolution. Dev. Genetics, 17: 188-197 (1995).
Munson, et al. Recovery of bisulphite-converted genomic sequences in the methylation-sensitive QPCR. Nucleic Acids Research (2007) 35(9): 2893-2903.
Narayan, et al. Frequent Promoter Methylation of CDH1, DAPK, RARB, and HIC1 Genes in Carcinoma of Cervix Uteri: Its Relationship to Clinical Outcome, Mol Cancer, 2(1): 24; May 2003, 12 pages.
NCBI Database Accession No. M24485, Dec. 5, 1994.
Newton, et al. "The production of PCR products with 5' single-stranded tails using primers that incorporate novel phosphoramidite intermediates." Nucleic Acid Res. 21(5): 1155-1162 (1993).
Nilsson, et al. Padlock Probes: Circularizing Oligonucleotides for localized DNA Detection. Science; 265: 2085-2088 (1994).
Nousbaum, et al. Prospective Characteristics of Full-Length Hepatitis C Virus NS5A Quasispecies during Induction and Combination Antiviral Therapy, J Virol., 74(19): 9028-9038 (2000).
Okada, et al. Sequence Determination of Rat U5 RNA Using a Chemical Modification Procedure for Counteracting Sequence Compression, (1982) J. Biochem. 91: 1281-1291.
Olek, et al. A modified and improved method for bisulphate based cytosine methylation analysis. (1996) Nucleic Acids Research, 24(24): 5064-5066.
Pao, et al. The endothelin receptor B (EDNRB) promoter displays heterogeneous, site specific methylation patterns in normal and tumor cells, Human Molecular Genetics, 10(9): 903-910, 2001.
Paris, et al. Probing DNA sequencs in solution with a monomer-excimer fluorescence color change. Nucleic Acids Research, 26(16):3789-3793 (1998).
Paulin, et al. Urea improves efficiency of bisulphite-mediated sequencing of 5'-methylcytosine in genomic DNA, Nucleic Acid Research, 26(21): 5009-5010 (Nov. 1, 1998).
Pietrobono, et al. Quantitative analysis of DNA demethylation and transcriptional reactivation of the FMR1 gene in fragile X cellstreated with 5-azadeoxycytidine. Nucleic Acids Research, 30(14): 3278-3285 (2002).
Raizis, et al. A Bisulfite method of 5-methylcytosine mapping that minimizes template degradation, Anal. Biochem., 226: 161-166 (1995).
Ratushna, et al. Secondary structure in the target as a confounding factor in synthetic oligomer microarray design, Genomics, 6(1): Mar. 31, 2005, 13 pages.
Rein, et al. Identifying 5-methylcytosine and related modifications in DNA genomes. Nucleic Acids Research, 26 (10): 2255-2264 (May 15, 1998).
Robertson, et al. DNA methylation: past, present, and future directions. Carcinogenesis. 21(3): 461-467 (2000).
Robertson, et al. Methylation of the Epstein-Barr Virus Genome in normal Lymphocytes, Blood, 90: 4480-4484 (1997).
Sakaguchi, et al. Cautionary Note on the Use of dUMP-Containing PCR Primers with Pfu and VentR® DNA Polymerases. Biotechniques; 21(3): 368 & 370 (1996).
Sakashita, et al. Dynamic DNA methylation change in the CpG island region of p15 during human myeloid development, J. Clin. Invest., 108: 1195-1204 (2001).
Shao-Qing. Chinese journal of Agricultureal Biotechnology, vol. 4, No. 1, pp. 75-79, 2007.
Shapiro et al., Specific Deamination of RNA by Sodium Bisulphite, Nature (1970) 227: 1047-1048.

(56) References Cited

OTHER PUBLICATIONS

Shapiro, et al. Deamination of cytosine derivatives by bisulfite. Mechanism of the reaction, J. Am. Chem. Soc., 96: 906-912 (1974).
Shibutani, et al., Translesional Synthesis on DNA Templates Containing a Single Abasic Site, J Biol Chem., 272(21): 13916-13922, 1997.
Shiraishi, et al. High Speed Conversion of Cytosine to Uracil in Bisulphite Genomic Sequencing Analysis of DNA Methylation; DNA Research,. 2: 409-415 (2004).
Stratagene, Gene Characterization Kit, 1988 Catalog, p. 39.
Tada, et al. Embryonic germ cells induce epigenetic reprogramming of somatic nucleus in hybrid cells. EMBO Journal, 16(21): 6510-6520 (1997).
Telenius, et al. Degenerate Oligonucleotide-Primed PCR: General Amplification of Target DNA by a Single Degenerate Primer, Genomics; 13(3): 718-725 (1992).
Timofeev et al. Methidium intercalator inserted into synthetic oligonucleotides. Tetrahedron Letters. 37(47):8467-8470 (1996).
Tohgi, et al. Decrease with age in methylcytosines in the promoter region of receptor for advanced glycated end products (RAGE) gene in autopsy human cortex, Molec Brain Res, 65: 124-128 (1999).
Toulmé et al. Specific inhibition of Mrna translation by complementary oligonucleotides covalently linked to intercalating agents. Proc Natl Acad Sci USA. 83:1227-1231 (1986).
Toyota, et al. Inactivation of *CACNA1G*, a T-Type Calcium Channel Gene, by Aberrant Methylation of Its 5' CpG Island in Human Tumors, Cancer Research, 59: 4535-4541, Sep. 1999.
Triplett, et al., Carbon-13 NMR Investigation of the bisulphite induced changes in yeast RNA; Biochemical and Biophysical Research Communications (1977), 77(4): 1170-1175.
Tsuda, et al. Relationship between HPV typing and abnormality of G1 cell cycle regulators in cervical neoplasm, Gynecologic Oncology, 91: 476-485, 2003.
Ushijima, et al. Aberrant methylations in cancer cells: Where do they come from? Cancer Science. 96(4): 206-211, Apr. 2005.
Venter, et al. The sequence of the human genome, Science, 291 (5523): 1304-1351 (2001).
Verma, Viral genes and methylation, Annals of the N. Y. Academy of Scuebces, 983: 170-180, Mar. 2003.
Virmani, et al. Aberrant Methylation during Cervical Carcinogenesis, Clin Cancer Res. 7(3): 584-489, Mar. 2001.
Wang et al. Comparison of bisulfite modification of 5-methyldeoxycytidine and deoxycytidine residues, Nucleic Acids Research, 8(2): 4777-4790 (1980).
Warnecke, et al. "Detection and measurement of PCR bias in quantitative methylation analysis of bisulphite-treated DNA," Nucleic Acids Research, vol. 25 No. 21, pp. 4422-4426, (1997).
Widschwendter et al: Analysis of aberrant DNA methylation and human papillomavirus DNA in cervicovaginal specimens to detect invasive cervical cancer and its precursors, Clin Cancer Res. 10(10): 3396-3400, May 2004.
Xiong, et al. COBRA: a sensititive and quantitative DNA methylation assay. (1997) Nucleic Acids Research, 25 (12): 2532-2534.
Yamana et al. Synthesis and properties of oligonucleotides bearing a pendant pyrene group. Nucleic Acids Research. 16:169-172 (1985).
Yamana et al. Oligonucleotides having covalently linked anthracene at specific sugar residue: Differential binding to DNA and RNA and fluorescence properties. Tetrahedron Letters. 36(46):8427-8430 (1995).
Yamana et al. Incorporation of two anthraquinonylmethyl groups into the 2'-O-positions of oligonucleotides: Increased affinity and sequence specificity of anthraquinone-modified oligonucleotides in hybrid formation with DNA and RNA. Bioconjugate Chem., 7:715-720 (1996).
Yamana et al. Synthesis of oligonucleotide derivatives containing pyrene labeled glycerol linkers: enhanced excimer fluorescence on binding to a complementary DNA sequence. Tetrahedron Letters. 38(34): 6051-6054 (1997).
Yamana et al. 2'-Pyrene modified oligonucleotide provides a highly sensitive fluorescent probe of RNA. Nucleic Acids Research. 27(11):2387-2392 (1999).
Yanagi, et al. "Hepatitis C Virus: An infectious molecular clone of a second major genotype (2a) and lack of viability of intertypic 1a and 2a chimeras," Virology 262(1): 250-263 (1999).
Yao, M. et al, "Further Characterization of *Escherichia coli* Endonuclease V", Journal of Biological Chemistry, 1997, vol. 272, No. 49, pp. 30774-30779.
Zeschnigk, et al. "A novel real-time PCR assay for quantitative analysis of methylated alleles (QAMA): analysis of the retinoblastoma locus," Nucleic Acid Res. 2004, 32(16): 1-5.
Office Action in U.S. Appl. No. 10/561,029 dated Apr. 13, 2009.
Office Action in U.S. Appl. No. 10/561,029 dated Dec. 8, 2009.
Notice of Allowance issued in U.S. Appl. No. 10/561,029 dated May 28, 2010.
Office Action in U.S. Appl. No. 10/555,465 dated Oct. 1, 2008.
Notice of Abandonment in U.S. Appl. No. 10/555,465 dated Jun. 2, 2009.
Office Action in U.S. Appl. No. 10/428,310 dated Jan. 4, 2006.
Office Action in U.S. Appl. No. 10/428,310 dated Jul. 5, 2006.
Office Action in U.S. Appl. No. 10/428,310 dated Aug. 31, 2006.
Office Action in U.S. Appl. No. 10/428,310 dated Nov. 3, 2006.
Notice of Allowance in U.S. Appl. No. 10/428,310 dated May 24, 2007.
Notice of Allowance in U.S. Appl. No. 10/428,310 dated Sep. 21, 2007.
Office Action in U.S. Appl. No. 12/413,380 dated Mar. 11, 2011.
Office Action in U.S. Appl. No. 12/413,380 dated Nov. 3, 2011.
Notice of Allowance in U.S. Appl. No. 12/413,380 dated Jan. 9, 2012.
Office Action in U.S. Appl. No. 10/416,637 dated May 4, 2006.
Notice of Abandonment in U.S. Appl. No. 10/416,637 dated Jun. 15, 2007.
Office Action in U.S. Appl. No. 10/499,479 dated Dec. 20, 2006.
Office Action in U.S. Appl. No. 10/499,479 dated Apr. 19, 2007.
Office Action in U.S. Appl. No. 10/499,479 dated Jan. 3, 2008.
Office Action in U.S. Appl. No. 10/499,479 dated May 2, 2008.
Office Action in U.S. Appl. No. 10/499,479 dated May 30, 2008.
Office Action in U.S. Appl. No. 10/499,479 dated Feb. 5, 2009.
Notice of Abandonment in U.S. Appl. No. 10/499,479 dated Nov. 6, 2009.
Office Action in U.S. Appl. No. 12/534,743 dated May 14, 2010.
Notice of Abandonment in U.S. Appl. No. 12/534,743 dated Jan. 5, 2011.
Office Action in U.S. Appl. No. 11/660,586 dated Sep. 15, 2009.
Office Action in U.S. Appl. No. 11/660,586 dated Apr. 15, 2010.
Office Action in U.S. Appl. No. 11/660,586 dated Aug. 6, 2010.
Office Action in U.S. Appl. No. 11/660,586 dated Jul. 20, 2011.
Notice of Abandonment in U.S. Appl. No. 11/660,586 dated Mar. 7, 2012.
Office Action in U.S. Appl. No. 10/536,633 dated Apr. 4, 2007.
Office Action in U.S. Appl. No. 10/536,633 dated Jan. 25, 2007.
Notice of Abandonment in U.S. Appl. No. 10/536,633 dated Jan. 18, 2008.
Office Action in U.S. Appl. No. 11/919,443 dated Feb. 2, 2012.
Office Action in U.S. Appl. No. 11/919,443 dated May 29, 2012.
Notice of Allowance in U.S. Appl. No. 11/919,443 dated Dec. 26, 2012.
Office Action in U.S. Appl. No. 10/543,017 dated Aug. 8, 2007.
Office Action in U.S. Appl. No. 10/543,017 dated Oct. 19, 2007.
Office Action in U.S. Appl. No. 10/543,017 dated Jun. 20, 2008.
Office Action in U.S. Appl. No. 10/543,017 dated Dec. 8, 2008.
Notice of Abandonment in U.S. Appl. No. 10/543,017 dated Jun. 26, 2009.
Office Action in U.S. Appl. No. 10/570,715 dated Dec. 14, 2009.
Office Action in U.S. Appl. No. 10/570,715 dated Apr. 15, 2010.
Notice of Allowance in U.S. Appl. No. 10/570,715 dated Jul. 30, 2010.
Office Action in U.S. Appl. No. 11/573,873 dated May 4, 2009.
Office Action in U.S. Appl. No. 11/573,873 dated Sep. 2, 2009.
Office Action in U.S. Appl. No. 11/573,873 dated Mar. 23, 2010.

(56) References Cited

OTHER PUBLICATIONS

Notice of Allowance issued in U.S. Appl. No. 11/573,873, mailed Jul. 1, 2010.
Office Action in U.S. Appl. No. 12/892,484, mailed Mar. 21, 2013.
Notice of Allowance issued in U.S. Appl. No. 12/892,484, mailed Aug. 29, 2013.
Notice of Allowance issued in U.S. Appl. No. 11/575,060, mailed Jun. 15, 2010.
Office Action in U.S. Appl. No. 11/756,534 dated Aug. 10, 2009.
Office Action in U.S. Appl. No. 11/756,534 dated Feb. 22, 2010.
Office Action in U.S. Appl. No. 11/756,534 dated Jun. 8, 2010.
Office Action in U.S. Appl. No. 11/756,534 dated Oct. 20, 2010.
Notice of Abandonment in U.S. Appl. No. 11/756,534 dated May 12, 2011.
Office Action in U.S. Appl. No. 12/531,482 dated Jan. 17, 2012.
Notice of Abandonment in U.S. Appl. No. 12/531,482 dated Aug. 28, 2012.
Office Action in U.S. Appl. No. 12/066,644 dated Apr. 22, 2010.
Office Action in U.S. Appl. No. 12/066,644 dated Sep. 23, 2010.
Office Action in U.S. Appl. No. 12/066,644 dated Mar. 13, 2012.
Notice of Allowance in U.S. Appl. No. 12/066,644 dated Aug. 31, 2012.
Notice of Abandonment in U.S. Appl. No. 12/227,962 dated Sep. 28, 2011.
Office Action in U.S. Appl. No. 12/744,310 dated Aug. 20, 2012.
Office Action in U.S. Appl. No. 12/744,310 dated Apr. 9, 2013.
Notice of Abandonment in U.S. Appl. No. 12/744,310 dated Nov. 18, 2013.
Office Action in U.S. Appl. No. 12/744,305 dated Aug. 21, 2012.
Office Action in U.S. Appl. No. 12/744,305 dated Mar. 28, 2013.
Office Action in U.S. Appl. No. 12/744,305 dated Oct. 7, 2013.
Notice of Allowance in U.S. Appl. No. 12/744,305 dated Nov. 18, 2013.
Office Action in U.S. Appl. No. 12/747,483 dated Jun. 26, 2012.
Office Action in U.S. Appl. No. 12/747,483 dated Oct. 7, 2013.
Notice of Abandonment in U.S. Appl. No. 12/747,483 dated Jun. 6, 2014.
International Search Report issued in PCT Application No. PCT/AU2004/000083, mailed Feb. 24, 2004.
International Search Report issued in PCT Application No. PCT/AU2004/000549, mailed Jul. 23, 2004.
International Search Report issued in PCT Application No. PCT/AU2004/000722, mailed Jun. 29, 2004.
International Search Report issued in PCT Application No. PCT/AU2004/001196, mailed Sep. 27, 2004.
International Search Report issued in PCT Application No. PCT/AU2006/000755, dated Aug. 30, 2006.
International Search Report issued in PCT Application No. PCT/AU2006/000698, dated Aug. 1, 2006.
International Preliminary Report on Patentability in PCT Application No. PCT/AU2006/000698, dated Apr. 20, 2007.
International Search Report issued in PCT Application No. PCT/AU2008/000367, dated May 14, 2008.
International Preliminary Report on Patentability in PCT Application No. PCT/AU2008/000367, dated May 6, 2009.
International Search report issued in PCT Application No. PCT/AU2008/001796, mailed Feb. 23, 2009.
International Search report issued in PCT Application No. PCT/AU2008/001751, mailed Feb. 18, 2009.
International Search Report issued in corresponding PCT Application No. PCT/AU2008/001891, mailed Feb. 3, 2009.
International Search Report mailed Mar. 18, 2010 for PCT Application No. PCT/AU2010/000055, filed Jan. 15, 2010.
International Preliminary Report of Patentability dated Oct. 11, 2010 for PCT Application No. PCT/AU2010/000055, filed Jan. 15, 2010.
International Search Report and Written Opinion dated Nov. 10, 2011 in Application No. PCT/AU2011/001156, filed Jul. 9, 2011.
International Preliminary Report on Patentability dated Mar. 12, 2014 in Application No. PCT/AU2011/001156, filed Jul. 9, 2011.
Extended European Search Report issued on Dec. 4, 2008 in European Application No. 05779000.8.
Extended European Search Report issued on Nov. 7, 2008 in European Application No. 05821631.8.
Extended European Search Report issued on Mar. 12, 2009 in European Patent Application No. EP 05813335.6.
Extended European Search Report issued on Aug. 7, 2009 in European Patent Application No. EP 06774977.0.
Extended European Search Report issued on Dec. 2, 2010 in European Patent Application No. EP 08853330.2.
Office Action in Chinese Patent Application No. 201180073300.7, dated Oct. 24, 2016.

\* cited by examiner

MOLECULAR DETECTION ASSAY USING DIRECT TREATMENT WITH A BISULPHITE REAGENT

RELATED APPLICATIONS

This application is the U.S. National Phase filing under 35 U.S.C. §371 of PCT/AU2011/001156, filed Sep. 7, 2011, entitled "Molecular Detection Assay", which designated the United States and was published in English on Mar. 14, 2013 as WO 2013/033749.

TECHNICAL FIELD

The present invention relates to methods for processing of samples for molecular detection assays, particularly processing clinical samples for nucleic acid detection assays for disease detection.

BACKGROUND OF THE INVENTION

Molecular testing of humans has become increasingly important for medical diagnosis and patient management. Molecular testing of animals is gaining importance in veterinary applications. Nucleic acid testing is an essential tool for modern forensics, immigration, paternity assignment, and other human identity applications. Epigenetics is becoming increasingly important for cancer research, identification of biomarkers, predisposition factors, and potential drug targets. RNA Genotyping encompasses a range of applications used to analyse genetic differences between individuals or cells, in all areas of research, applied testing, and diagnostics. When dealing with biological samples, present molecular tests require specific pre-treatment of the samples prior to carrying out nucleic acid detection with techniques such as polymerase chain reaction (PCR). Sample pre-treatment is presently considered essential and many commercial kits and systems have been developed and are being used in the marketplace. Unfortunately, pre-treatment adds a costs to molecular testing and requires additional processing time and equipment.

Human Genetic Signatures Pty Ltd (Sydney, Australia) has developed a method for detection of microorganisms as disclosed in WO 2006/058393 and U.S. Pat. No. 7,833,942. The method involves treating microbial nucleic acid of a microorganism with an agent to form a simplified form of nucleic acid derived from the microbial nucleic acid having unique nucleic acid sequences that can be used to detect the microorganism.

The present inventor has developed an improved molecular detection assay that does not require sample pre-treatment as presently required in molecular detection assays.

SUMMARY OF THE INVENTION

The present invention relates to a molecular detection assay carried out on a biological sample without requiring a sample clean-up step or processing of the biological sample to lyse cells or purify nucleic acid.

In a first aspect, the present invention provides a molecular detection assay comprising:

(a) treating a biological sample directly with a bisulphite agent under conditions that allow cell disruption and nucleic acid treatment;

(b) removing the bisulphite agent from the treated sample; and (c) detecting a target nucleic acid in the treated sample.

The biological sample does require cellular disruption or chemical/physical treatment prior to step (a).

The biological sample may be selected from faecal, nasal, blood, plasma, serum, buccal cells, pus, wound, concentrated filtrates, cerebrospinal fluid, semen, liquid based cytology (LBC), tissue, FFPE, laser captured cells, cultured cells, pelleted cells, bacterial cultures, bacterial colonies, viral suspension, aspirate, bronchial lavage, sputum sample, environmental sample, environmental concentrate, foodstuff, raw ingredient, water sample or water concentrate, and the like.

The nucleic acid detected may be DNA, RNA or combinations of both DNA and RNA.

The assay is suitable for detecting infectious disease, genetic disease or genetic trait in an animal. Preferably, the animal is a human.

The infectious disease may be caused by a microorganism including bacteria, viruses, viroid, yeast, fungi, prion, parasites, or amoeba.

The genetic disease may be cancer, mutation, copy number variation, inherited disorder, environmental induced disease, disease caused by exposure to carcinogens, disease characterised by expansion or reduction in a nucleotide repeat length in a genome.

The genetic trait may be susceptibility to cancer or any other disease where genetic and epigenetic changes contribute to the development of a disease state.

Preferably the bisulphite agent is sodium bisulphite or sodium metabisulphite. The bisulphite agent is preferably used at a concentration of about 2.5M to about 3.5M having a pH range of about 4.5 to about 5.5. More preferably, the bisulphite agent is used at a concentration of about 3M at a pH of about 5.0.

Preferably, step (a) involves heating between about 75° C. and 95° C. for about 1 minute to 30 minutes. More preferably, the sample is heated for about 10 to 20 minutes at a temperature of between about 80° C. and 95° C. It will be appreciated that the temperature and heating duration may vary depending on the sample being treated and the cellular source of the nucleic acid to be detected.

The bisulphite can be removed from the treated sample by any suitable means. Examples include column based purification or bead based purification are optimal but in some cases a simple precipitation step may be sufficient.

After removal of the bisulphite, the sample is preferably resuspended in elution buffer which has a pH of at least 10, more preferably between about pH 11.5 to about 12.5. A pH of at least about 12 has been found to be suitable for most samples.

The bisulphite agent modifies cytosine to uracil in treated nucleic acid. In double stranded DNA, the bisulphite agent modifies cytosine to uracil in each strand of complementary double stranded genomic DNA forming two derivative but non-complementary nucleic acid molecules.

In one preferred form, the derivative microbial nucleic acid substantially contains bases adenine (A), guanine (G), thymine (T) and uracil (U) and has substantially the same total number of bases as the corresponding untreated nucleic acid.

If the treated nucleic acid is amplified, then the amplified nucleic acid contains substantially the bases adenine (A), guanine (G) and thymine (T). The amplification may be carried out by any suitable means such as polymerase chain reaction (PCR), isothermal amplification, or signal amplification.

In a preferred form, the assay further includes providing nucleic acid primers or probes to the treated sample.

Preferably the treated sample undergoes an amplification reaction to form a target nucleic acid molecule specific for the microorganism or genetic indicator.

The target nucleic acid molecule is preferably detected by amplification. Examples of suitable amplification detection includes PCR, qPCR, Reverse transcriptase PCR, digital PCR, isothermal amplification or signal amplification.

The treated nucleic acid may also be detected by a sequencing method such Roche 454, ABI SOLiD or Ion torrent systems, Illumina Hi Seq SBS technology, Helicos Heliscope or SMRT technology employed by Pacific Biosciences or any other equivalent technology.

In a preferred form, the target nucleic acid molecule is detected by:

providing a detector ligand capable of binding to a target region of the microbial-specific nucleic acid molecule and allowing sufficient time for the detector ligand to bind to the target region; and measuring binding of the detector ligand to the target region to detect the presence of the microbial-specific nucleic acid molecule.

In another preferred form, the target nucleic acid molecule is detected by separating an amplification product and visualising the separated product. Preferably, the amplification product is separated by electrophoresis and detected by visualising one or more bands on a gel.

Preferably, the target nucleic acid molecule does not occur naturally in a cell.

In a second aspect, the present invention provides a kit for a molecular detection assay for direct treatment of a sample, the kit comprising:

a bisulphite reagent;
nucleic acid elution and reaction reagents;
PCR primers for the target nucleic acid; and
instructions to carry out the assay.

The kit may further include nucleic acid separation or purification columns, PCR mastermix, reagents for PCR, control nucleic acid primers, reaction tubes, test tubes, swabs, and the like.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form component of the prior art base or were common general knowledge in the field relevant to the present invention as it existed in Australia prior to development of the present invention.

In order that the present invention may be more clearly understood, preferred embodiments will be described with reference to the following drawings and examples.

MODE(S) FOR CARRYING OUT THE INVENTION

Advantages

The present invention has many advantages over the prior art methods including the following.

a. Lysis of the cells and nucleic acid conversion of the sample occurs simultaneously in the same tube and complete lysis and conversion can be achieved in less than 30 minutes, and even can be achieved by little as 10-20 minutes.

b. Samples such as faecal material can be directly processed without loss of sensitivity.

c. Tests based on the present invention have an advantage of being able performed on a primary patient sample without pre-treatment with enzymes such as proteinase K.

d. The method does not require any expensive purification methods such as commercial purification kits presently on the market. These commercial kits are available for just about every sample type such as blood, faeces, cultured cells, FFPE, bacteria, viruses and parasites to name but a few. These commercial kits can cost thousands of dollars and can take 2-4 hours to purify a sample. Just about every lab in the world uses these kits for sample purification prior to any subsequent amplification step in molecular assays presently employed.

e. After removal of the bisulphite the sample is then resuspended in a simple elution buffer that does not require any further treatment such as heat desulphonation, thus simplifying the process.

f. The method can simultaneously detect both RNA and DNA viruses in the same tube from the same sample without any need to use a specialised viral purification kit. Both RNA and DNA viruses (even although one is single stranded and one is double stranded) are lysed and converted with equal efficiency by the present invention.

g. Surprisingly the elution buffer, which is at high pH, does not degrade RNA. This finding goes against what has been taught in the prior art as prior art teaching specifically advises against the treatment of RNA at both high temperatures and pH.

h. The method can lyse and convert all bacterial types using similar conditions thus a single patient sample can be used for multiple tests for *C. difficile, Salmonella, Camplylobacter* and parasites, etc thus removing the problem of a separate extraction method for each bacteria or target microorganism.

i. The method is applicable to difficult to lyse samples such as parasites, which can form a tough outer shells that make them resistant to conventional lysis techniques. Thus target organisms such as *Mycobacterium tuberculosis* (TB) (very resistant to conventional lysis techniques) would be ideal to detect, as sensitive nucleic acid based diagnostic tests are required.

j. The method is able to efficiently lyse and convert hepatitis C virus (HCV) directly from serum using as few as 10 copies of the virus demonstrating the utility to detect important RNA viruses at a very low level.

k. The method also reduces sample processing time by many hours and removes the problem that the sample had to be purified then bisulphite converted and purified again as presently carried out.

l. The method is suitable for the sensitive detection of colorectal cancer in patient faecal material. Such samples are non-invasive and would reduce the reliance on endoscopy as the primary means of detection. In addition, a 'sample to result' would be expected in less than three hours without complex sample processing procedure. The use of faecal material over serum samples for diagnosis has many advantages the most significant is that a high number of human cells are likely to be present in the sample, unlike serum samples where sensitivity is always a major problem.

Samples

The present invention is suitable for processing samples including faecal, nasal, blood, plasma, serum, buccal cells, pus, wound, concentrated filtrates, cerebrospinal fluid, semen, liquid based cytology (LBC), tissue, FFPE, laser captured cells, cultured cells, pelleted cells, bacterial cultures, bacterial colonies, viral suspension, aspirate, bronchial lavage, sputum sample, environmental sample, environmental concentrate, foodstuff, raw ingredient, water sample, water concentrate or the like.

Sample Treatment (HGS)

A preferred method of treating a sample according to the present invention is as follows. The sample is placed directly into 200 µl of 3M (range 2.5 to 3.5M) sodium bisulphite pH 5.0 (pH range 4.5 to 5.5) and heated at between 75° C. and 95° C. for between 10 and 20 minutes.

The bisulphite is removed from the treated sample by any suitable means. Examples include column based purification or bead based purification are optimal but in some cases a simple precipitation step may be sufficient.

After removal of the bisulphite, the sample is resuspended in elution buffer which has a pH of between 11.5 to 12.5 (>pH 12 preferred).

The sample is now ready for PCR amplification without further processing.

Removal of Bisulphite

Bisulphite removal can be used achieved by a commercially available method such as the MethylEasy™ technique (Human Genetic Signatures). Briefly, 240 µl of reagent #3 is added to the sample and the sample transferred to a centrifuge column. The column is then spun at 10,000×g to remove the bisulphite. The column is then washed ×2 with 300 µl of reagent #4 spinning at 10,000×g between washes. 20 to 50 µl of elution buffer is added and the sample spun into a clean collection tube. The sample is now ready for PCR amplification.

Sample Pre-Treatment

Current sample pre-treatment involves commercial kits sold by Qiagen Inc (Valencia, Calif. 91355 USA), Sigma Life Sciences (St Louis, Mo., USA), Invitrogen Corporation (Carlsbad, Calif. 92008, USA), and Promega Corporation (Madison, Wis. 53711 USA).

The present invention was compared with the following methods.

"In-House" Hospital Test

A sample of stool was heated at 95° C. for 10 minutes then diluted and the sample then amplified for the tcdB gene of C. difficile.

Qiagen Purification

QIAamp DNA Stool Mini Kit (50) Cat #51504.

Commercial Parasite Test

AusDiagnostics Gastrointestinal Parasites 5, Catalogue number: 6502.

Results

Faecal Samples

All faecal samples tested in Tables 1, 2, 3 and 4 were treated as follows:

A swab was placed in faecal material and then transferred to a tube containing 200 µl of 3M sodium bisulphite pH 5.0 mixed and then heated at 95° C. for 15 minutes.

Bisulphite was removed using the MethylEasy™ method and the samples were resuspended in 20-50 µl of elution buffer then amplified using standard conditions.

Table 1 shows the results of an "in-house" hospital test, the same samples tested using Qiagen purification and the same samples tested using the method according to the present invention. As can be seen from the results the "in-house" hospital test resulted in 7 false negative results and 1 false positive result (confirmed by EIA and culture as well as a commercially available molecular diagnostic kit) indicating that the method did not have the required sensitivity for the detection of C. difficile in primary patient samples. Using the Qiagen method, 4 samples did not have enough material for processing while 1 sample gave a false negative result (GDH positive by EIA). These results demonstrate the utility of the method according to the present invention (HGS method) for the rapid diagnosis of C. difficile. In addition, samples that have limited volumes are easily assayed using the HGS method. In addition, the Qiagen method requires at least 2 hours sample preparation time and having to weigh out predetermine amounts of faecal material.

TABLE 1

Results of the "in-house" hospital test vs Qiagen purification vs HGS method for the detection of C. difficile.

| Sample# | "In-house" | Qiagen | HGS |
|---|---|---|---|
| 1 | NEG | NEG | NEG |
| 2 | POS | POS | POS |
| 3 | NEG | NEG | POS |
| 4 | POS | POS | POS |
| 5 | POS | POS | POS |
| 6 | NEG | NEG | NEG |
| 7 | POS | POS | POS |
| 8 | NEG | POS | POS |
| 9 | NEG | NEG | NEG |
| 10 | NEG | NEG | NEG |
| 11 | NEG | NEG | NEG |
| 12 | NEG | POS | POS |
| 13 | NEG | NEG | NEG |
| 14 | NEG | NEG | NEG |
| 15 | POS | NEG | NEG |
| 16 | NEG | NEG | NEG |
| 17 | NEG | NEG | NEG |
| 18 | NEG | INSUFF | NEG |
| 19 | NEG | NEG | NEG |
| 20 | NEG | POS | POS |
| 21 | POS | POS | POS |
| 22 | POS | POS | POS |
| 23 | NEG | NEG | NEG |
| 24 | NEG | POS | POS |

TABLE 1-continued

Results of the "in-house" hospital test vs Qiagen purification vs HGS method for the detection of C. difficile.

| Sample# | "In-house" | Qiagen | HGS |
|---|---|---|---|
| 25 | POS | INSUFF | POS |
| 26 | NEG | NEG | NEG |
| 27 | NEG | POS | POS |
| 28 | NEG | NEG | NEG |
| 29 | NEG | NEG | NEG |
| 30 | NEG | NEG | NEG |
| 31 | POS | INSUFF | POS |
| 32 | POS | POS | POS |
| 33 | NEG | NEG | NEG |
| 34 | NEG | NEG | NEG |
| 35 | NEG | NEG | NEG |
| 36 | NEG | NEG | NEG |
| 37 | NEG | NEG | NEG |
| 38 | NEG | POS | POS |
| 39 | POS | POS | POS |
| 40 | POS | POS | POS |
| 41 | POS | POS | POS |
| 42 | POS | POS | POS |
| 43 | POS | INSUFF | POS |
| 44 | NEG | NEG | NEG |
| 45 | NEG | NEG | NEG |

TABLE 2

Results of the Standard microscopy vs commercially available parasite detection kit vs HGS method.

| Sample# | Parasite Detected | EasyPlex Gastrointestinal Parasites 5 | HGS | Other Clinical Results |
|---|---|---|---|---|
| 1 | Giardia intestinalis | Negative | Giardia intestinalis | |
| 2 | Giardia intestinalis | Negative | Giardia intestinalis | |
| 3 | Giardia intestinalis | Negative | Giardia intestinalis | |
| 4 | Cryptosporidium spp. | Negative | Cryptosporidium spp | |
| 5 | Cryptosporidium spp. | Negative | Cryptosporidium spp | |
| 6 | Cryptosporidium spp. | Negative | Cryptosporidium spp | |
| 7 | Giardia intestinalis | Negative | Giardia intestinalis | |
| 8 | Giardia intestinalis | Negative | Giardia intestinalis | |
| 9 | Giardia intestinalis | Negative | Giardia intestinalis | |
| 10 | Cryptosporidium spp. | Cryptosporidium spp. | Cryptosporidium spp and Entamoeba | |
| 11 | Cryptosporidium spp. | Cryptosporidium spp. | Cryptosporidium spp. | |
| 12 | Cryptosporidium spp. | Cryptosporidium spp. | Cryptosporidium spp. | |
| 13 | Giardia intestinalis | Negative | Giardia intestinalis and Entamoeba | |
| 14 | Giardia intestinalis | Cryptosporidium spp. | Giardia intestinalis and Entamoeba | |
| 15 | Giardia intestinalis | Negative | Giardia intestinalis and Entamoeba | |
| 16 | Giardia intestinalis | Negative | Giardia intestinalis | |
| 17 | Giardia intestinalis | Negative | Giardia intestinalis | |
| 18 | D. fragilis, G. lamblia | Cryptosporidium spp. | Giardia intestinalis, Dientamoeba and Salmonella spp. | Salmonella Isolated |
| 19 | Giardia intestinalis | Giardia | Giardia intestinalis | |
| 20 | Giardia intestinalis | Negative | Giardia intestinalis | |
| 21 | Giardia intestinalis | Cryptosporidium spp. | Giardia intestinalis | |
| 22 | Cryptosporidium spp. | Cryptosporidium spp. | Cryptosporidium spp. | |
| 23 | Giardia intestinalis | Negative | Giardia intestinalis, Dientamoeba and Campy | C. jejuni Isolated |
| 24 | Giardia intestinalis | Negative | Giardia intestinalis | |
| 25 | Giardia intestinalis | Negative | Giardia intestinalis | |
| 26 | Giardia intestinalis | Negative | Giardia intestinalis | |
| 27 | NPI | Negative | Negative | |
| 28 | NPI | Negative | Negative | |
| 29 | NPI | Negative | Negative | |
| 30 | Cryptosporidium spp. | Cryptosporidium spp. | Cryptosporidium spp. and Shigella | No Shigella Isolated |
| 31 | Cryptosporidium spp. | Cryptosporidium spp. | Cryptosporidium spp. and Shigella | No Shigella Isolated |
| 32 | Cryptosporidium spp. | Cryptosporidium spp. | Cryptosporidium spp. and Shigella | No Shigella isolated |
| 33 | Cryptosporidium spp. | Cryptosporidium spp. | Cryptosporidium spp. and Shigella | No Shigella Isolated |
| 34 | Cryptosporidium spp. | Cryptosporidium spp. | Cryptosporidium spp. and Shigella | No Shigella Isolated |
| 35 | Cryptosporidium spp. | Cryptosporidium spp. | Cryptosporidium spp. | |
| 36 | Giardia intestinalis | Giardia | Giardia intestinalis, Entamoeba, Shigella | Shigella spp also isolated. |

TABLE 2-continued

Results of the Standard microscopy vs commercially available parasite detection kit vs HGS method.

| Sample# | Parasite Detected | EasyPlex Gastrointestinal Parasites 5 | HGS | Other Clinical Results |
|---|---|---|---|---|
| 37 | Giardia intestinalis | Negative | Giardia intestinalis | |
| 38 | Giardia intestinalis | Giardia | Giardia intestinalis, Entamoeba, Shigella | Shigella spp also isolated. |
| 39 | Giardia intestinalis | Giardia | Giardia intestinalis, Entamoeba, Shigella | Shigella spp also isolated. |
| 40 | NPI | Negative | Negative | |
| 41 | NPI | Negative | Giardia intestinalis | |
| 42 | NPI | Negative | Negative | |
| 43 | NPI | Negative | Giardia intestinalis | |
| 44 | Giardia intestinalis | Negative | Giardia intestinalis | |
| 45 | Giardia intestinalis | Negative | Giardia intestinalis | |
| 46 | NPI | Negative | Giardia intestinalis | |
| 47 | NPI | Negative | Giardia intestinalis | |
| 48 | NPI | Negative | Giardia intestinalis | |
| 49 | Giardia intestinalis | Negative | Giardia intestinalis | |
| 50 | Giardia intestinalis | Negative | Giardia intestinalis | |
| 51 | Giardia intestinalis | Negative | Giardia intestinalis | |
| 52 | NPI | Negative | Salmonella spp | Not Cultured |
| 53 | Giardia intestinalis | Negative | Giardia intestinalis | |
| 54 | Giardia intestinalis | Giardia | Giardia intestinalis | |

All the samples highlighted belong to the same patient.

Table 2 shows the results of a direct comparison of the standard microscopy, a commercial parasite test (Ausdiagnostic Easy-Plex Gastrointestinal parasite 5) and the HGS method. As can be seen from the results, the commercial method is unable to lyse many of the samples that contain the Giardia cysts. This is in contrast to the HGS method that easily detects all Giardia samples and also some samples that are missed by conventional microscopy. In addition, the HGS method seems to be universal for the lysis of bacteria and parasites alike as a number of samples contained both parasites and bacteria, results that were subsequently confirmed by the hospital.

Table 3 shows the results of the HGS method vs conventional culture methods for microbial detection. As can be seen the culture method failed to detect one sample that contained A Campylobacter spp that the molecular method detected. In addition no cross-reactivity was detected with samples that contained C. difficile. All positive culture results agreed with the HGS method indicating the improved sensitivity of molecular methods compared to conventional culture. Furthermore, the results of the HGS method are available in as little as 3 hours compared to overnight cultures required for conventional culture methods.

TABLE 3

Results of conventional culture methods for the detection of enteric bacterial vs the HGS method

| Sample | Culture | Campy | Salmon |
|---|---|---|---|
| A01 | Salmon | N/A | 23.77 |
| A02 | NPI | N/A | N/A |
| A03 | Salmon | N/A | 29.7 |
| A04 | Salmon | N/A | 26.06 |
| A05 | Campy | 39.18 | N/A |
| A06 | Campy | 44.37 | N/A |
| A07 | Campy | 39.88 | N/A |
| A08 | Salmon | N/A | 39.83 |
| A09 | CD | N/A | N/A |
| A10 | Campy | 35.39 | N/A |
| A11 | NPI | 36.09 | N/A |
| A12 | Campy | 35.72 | N/A |
| A13 | Salmon | N/A | 30.21 |
| A14 | Salmon | N/A | 30.24 |
| A15 | Campy | 40.05 | N/A |
| A16 | Salmon | N/A | 27.06 |
| A17 | Campy | 36.26 | N/A |
| A18 | Campy | 44.81 | N/A |
| A19 | Campy | 26.57 | N/A |
| A20 | Campy | 29.8 | N/A |
| A21 | Salmon | N/A | 26.58 |
| A22 | Campy | 34.78 | N/A |
| A23 | Campy | 32.57 | N/A |
| A24 | Salmon | N/A | 30.98 |
| A25 | Campy | 31.18 | N/A |
| A26 | Salmon | N/A | 45.32 |
| A27 | Campy | 41.49 | N/A |
| A28 | Campy | 38.69 | N/A |
| A29 | Campy | 38.36 | N/A |
| A30 | Salmon | N/A | 38.3 |
| A31 | CD | N/A | N/A |
| A32 | Salmon | N/A | 35.76 |
| A33 | Campy | 35.61 | N/A |
| A34 | CD | N/A | N/A |
| A35 | Campy | 36.12 | N/A |
| A36 | Campy | 39.96 | N/A |
| A37 | Salmon | N/A | 37.53 |
| A38 | Campy | 46.2 | N/A |
| A39 | Campy | 35.96 | N/A |
| A40 | Campy | 47.31 | N/A |
| A41 | Salmon | N/A | 30.3 |
| A42 | Salmon | N/A | 37.14 |
| A43 | CD | N/A | N/A |

Treatment Conditions

Figure 1:
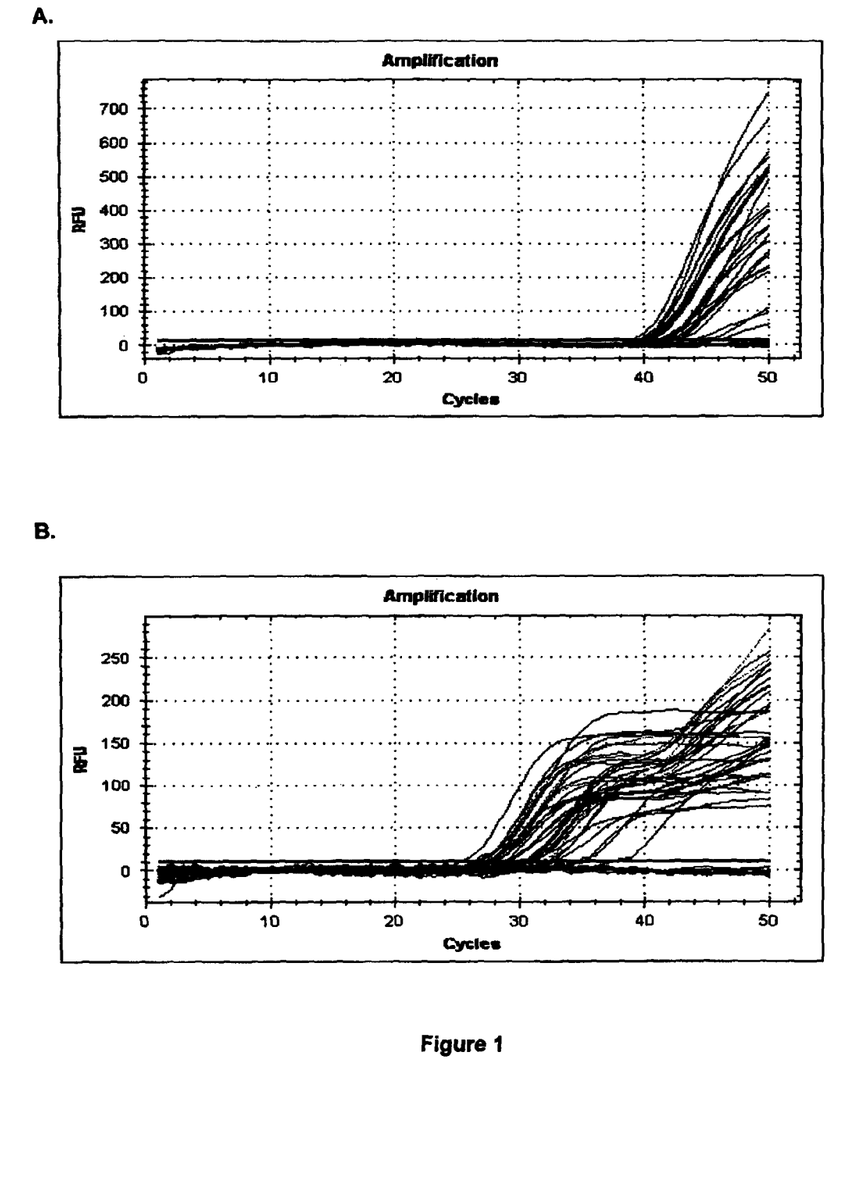
FIG. 1 shows results of *C. difficile* detection using the present invention. A. the Fam channel is specific for the tcdA/B genes of *C. difficile*; B. the Cy5 channel is specific for the extraction control.

Four stool samples, 3 positive for C. difficile and 1 negative for C. difficile were assayed to determine the effect of temperature and time on the extraction efficiency. An extraction control (16s rDNA gene) was also included to determine the effect of conditions on the mixed flora that is present within stool samples. The Fam channel is specific for the tcdA/B genes of *C. difficile* while the Cy5 channel is specific for the extraction control. The results are shown in FIG. 1 and Table 4.

As can be seen from the results in Table 4 the preferred temperature and times for lysis of these samples lie between 85° C.-95° C. for 15 minutes. All positive samples and faecal flora were easily detected.

TABLE 4

The effect of time and temperature on the efficiency of the HGS lysis/conversion method using stool samples.

|  | tcdA/B | ExCon | tcdA/B | ExCon | tcdA/B | ExCon |
|---|---|---|---|---|---|---|
|  | 10 min/85° C. | | 15 min/85° C. | | 20 min/85° C. | |
| Sample 1 | 44.73 | 34.54 | 40.46 | 31.91 | 39.1 | 31.08 |
| Sample 2 | 41.57 | 35.09 | 41.59 | 30.31 | 40.23 | 29.09 |
| Sample 3 | N/A | 32.76 | N/A | 28.15 | N/A | 27.25 |
| Sample 4 | 42.6 | 30.19 | N/A | 30.26 | 46.22 | 28.91 |
|  | 10 min/90° C. | | 15 min/90° C. | | 20 min/90° C. | |
| Sample 1 | 41.66 | 32.17 | 39.63 | 30.39 | 39.88 | 30.73 |
| Sample 2 | 41.19 | 29.05 | 41.25 | 27.53 | 41.33 | 25.17 |
| Sample 3 | N/A | N/A | N/A | 27.31 | N/A | 26.6 |
| Sample 4 | 42.63 | 28.69 | 43.88 | 27.27 | N/A | 27.86 |
|  | 10 min/95° C. | | 15 min/95° C. | | 20 min/95° C. | |
| Sample 1 | 40.48 | 30.82 | 39.53 | 31.52 | 39.52 | 29.74 |
| Sample 2 | 40.38 | 26.41 | 40.3 | 26.31 | 42.21 | 30.52 |
| Sample 3 | N/A | 27.08 | N/A | 27.47 | N/A | 37.35 |
| Sample 4 | 41.93 | 27.64 | 40.31 | 27.76 | 42.2 | 26.66 |

TABLE 5

The effect of elution buffer pH on the ability of the method to efficiently detect HCV directly from serum samples

|  | 70° C. | | | 75° C. | | | 80° C. | | | 90° C. | | |
|---|---|---|---|---|---|---|---|---|---|---|---|---|
|  | 5 min | 10 min. | 15 min | 5 min | 10 min | 15 min | 5 min | 10 min | 15 min | 5 min | 10 min | 15 min |
| PCR-A-pH 11.5 | N/A | N/A | N/A | N/A | N/A | N/A | N/A | N/A | N/A | N/A | N/A | N/A |
| PCR-A-pH 12.5 | N/A | 36.83 | 36.01 | N/A | 33.27 | 34.8 | 36.88 | 33.02 | N/A | 34.45 | 34.22 | 33.14 |
| PCR-B-pH 11.5 | N/A | N/A | N/A | N/A | N/A | N/A | N/A | N/A | N/A | N/A | N/A | N/A |
| PCR-B-pH 12.5 | N/A | 39.34 | 37.17 | N/A | 35.76 | 36.2 | 40.98 | 35.05 | N/A | 36.21 | 36.48 | 35.51 |

10 μl of HCV (Acrometrix) were added to 200 μl of 3M sodium bisulphite and heated to 75° C., 75° C., 80° C. and 90° C. for 5, 10 or 15 minutes. Bisulphite was removed using a modified MethylEasy™ method and the samples were resuspended in 20 μl of elution buffer, 12 μl reverse transcribed then 2 μl amplified using standard conditions.

As can be seen from the results of Table 5 HCV RNA can easily withstand lysis conversion at 90° C., the highest temperature tested. Even more surprisingly the assay worked for RNA virus detection in the presence of the high pH buffer, which is contrary to the published literature indicating that RNA species need to be maintained around neutral pH.

These results combined with the results in Table 4 suggest that a temperature around 90° C. for 15 minutes could be a universal sample processing method for double stranded DNA containing organisms such as *C. difficile* and single stranded RNA viruses such as HCV. In addition, as *C. difficile* is a spore-containing organism the results indicate that the method is harsh enough to break open tough spores but gentle enough so that RNA containing viruses are not degraded. Again such data would not have been predicted by the prior art.

PCR A and B differ in the mastermix used (JumpStart (Sigma) and FastStart (Roche) respectively).

Serum

Dilutions of HCV (Zeptoometrix) were prepared then 10 μl of each dilution added to 200 μl of 3M sodium bisulphite and heated to 75° C. for 10 minutes.

Bisulphite was removed using the MethylEasy™ method and the samples were resuspended in 20 μl of elution buffer, 12 μl reverse transcribed then 2 μl amplified using standard conditions.

TABLE 6

Sensitive detection of HCV virus directly from serum.

|  | HCV/PCR | IU/PCR | Positive |
|---|---|---|---|
| 1\10 | 200 | 32.54 | 34.41 |
| 1\100 | 20 | 37.07 | 38.32 |
| 1\1000 | 2 | 37.54 | 38.63 |
| 1\10000 | 0.2 | N/A | N/A |
| 1/100000 | 0.02 | N/A | N/A |
| Process |  | N/A | N/A |

As can be seen from Table 6 when using the HGS method to process the serum directly, as few as 2 IU of HCV can de efficiently lysed and converted simultaneously. These results demonstrate the excellent sensitivity that can be generated using RNA viruses as a target for the process.

Table 7 simultaneous lysis/conversion of both RNA viruses and DNA viruses under identical extraction conditions.

Figure 2:
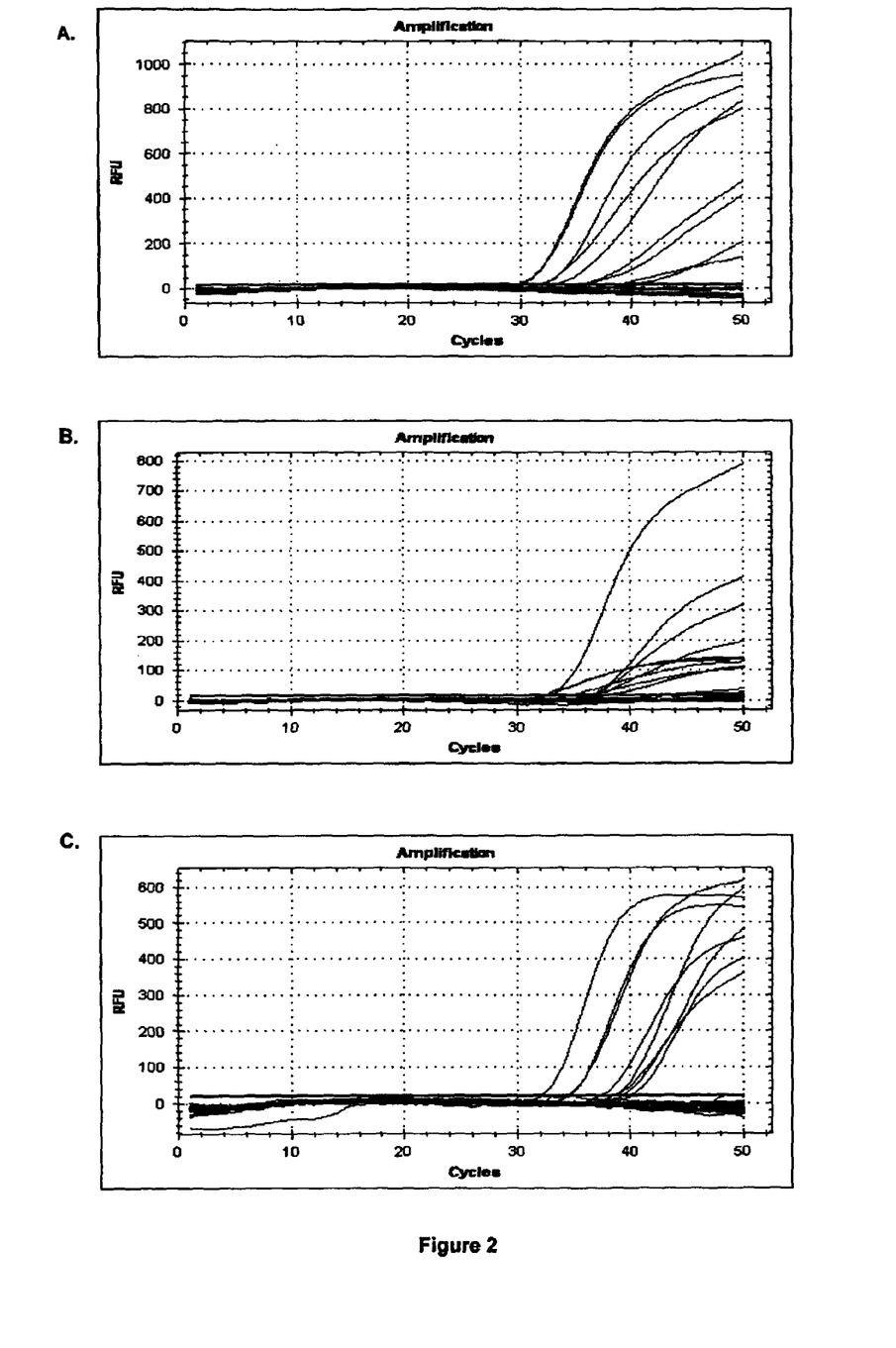
FIG. 2 shows results of amplification of the three viruses from the same sample. A. Fam=Norovirus (single stranded RNA virus); B. Hex=Adenovirus (double stranded DNA virus; C. Cy5=Rotavirus (single stranded RNA virus FIG. 3 shows the effect of spiking human cells into faecal material. A. shows human MRC5 cells heated for 15 minutes in 3M bisulphite reagent at 95° C. then resuspended in high pH buffer (12.3) and amplified for the human R-globin gene. B. shows the same cells spiked into faecal material heated for 15 minutes in 3M bisulphite reagent at 95° C. then resuspended in high pH buffer (12.3) and amplified for the human R-globin gene.

FIG. 2 shows amplification of the three viruses from the same sample.

A. Fam=Norovirus (single stranded RNA virus).

B. Hex=Adenovirus (double stranded DNA virus)

C. Cy5=Rotavirus (single stranded RNA virus)

Norovirus, Adenovirus and Rotavirus qualitative samples were obtained from Zeptometrix. Samples of each virus (10 μl) were added to 3M sodium bisulphite and the samples heated at 90° C. for 10, 15 and 20 minutes. The bisulphite was then removed using a modified MethylEasy™ method and the samples were resuspended in 20 μl of elution buffer, 12 μl reverse transcribed then 2 μl amplified using standard conditions.

As can be seen from Table 7 after 15 minutes heating at 90° C. both the RNA and DNA viruses are efficiently lysed and converted. Both virus types were purified under identical conditions. These results demonstrate further the utility of the HGS method as a universal sample preparation method for the lysis and efficient conversion of both DNA and RNA viruses from the same sample. Again surprisingly the RNA viruses can easily withstand the 90° C. sample treatment and high pH buffer.

TABLE 7

Simultaneous lysis/conversion of both RNA viruses and DNA viruses under identical extraction conditions.

| | Fam Norovirus | | | | Hex Adenovirus | | | | Cy5 Rotavirus | | | |
|---|---|---|---|---|---|---|---|---|---|---|---|---|
| | 10 min | 15 min | 20 min | PC | 10 min | 15 min | 20 min | PC | 10 min | 15 min | 20 min | PC |
| Neat | 31.75 | 29.67 | 30.09 | N/A | 36.32 | 32.36 | 36.37 | N/A | 34.5 | 32.13 | 37.35 | N/A |
| 1\10 | 35.61 | 33.25 | 31.96 | N/A | N/A | 36.45 | N/A | N/A | 40.04 | 34.5 | 38.6 | N/A |
| 1\100 | 40.51 | 38.87 | 35.84 | N/A | N/A | 44.67 | N/A | N/A | 39.32 | 38.57 | N/A | N/A |

Faecal samples were spiked with Norovirus, Adenovirus and Rotavirus qualitative samples obtained from Zeptometrix. Samples of virus (10 µl) were spiked into faecal material and the sample mixed. A swab was placed in faecal material and then transferred to a tube containing 200 µl of 3M sodium bisulphite pH 5.0 and then heated at 90° C. for 15 minutes.

Bisulphite was removed using a modified MethylEasy™ method and the samples were resuspended in 20 µl of elution buffer, 12 µl reverse transcribed then 2 µl amplified using standard conditions.

Table 8 the effect of spiking faecal samples with virus.

| | Norovirus | Adenovirus | Rotavirus | Process |
|---|---|---|---|---|
| Adenovirus spike | N/A | 41.1 | N/A | N/A |
| Norovirus spike | 39.45 | N/A | N/A | N/A |
| Rotavirus spike | N/A | N/A | 39.62 | N/A |

The results from Table 8 show that even when viral particles are spiked into faecal samples and the universal condition applied both DNA and RNA viruses are effectively lysed and converted. Thus the method should be applicable to any sample type for any micro-organism of interest.

Human Cells

To determine whether the present invention is also suitable for detection of human disease such as cancer, 5 µl, 10 µl and 20 µl of diluted human cells were incubated for 10 minutes or 15 minutes at 70° C., 80° C., 90° C. and 95° C. in 200 µl of 3M bisulphite. The samples were processed to remove the bisulphite solution and resuspended in 50 µl of buffer pH 12.3. Material (2 µl) was then amplified using primers and probes specific for the human β-globin gene. The results are shown in Table 9 and FIG. 3.

TABLE 9

Time/temperature optimisation using human MRC5 cells

| | 70° C. | | 80° C. | | 90° C. | | 95° C. | |
|---|---|---|---|---|---|---|---|---|
| | 10 min | 15 min | 10 min | 15 min | 10 min | 15 min | 10 min | 15 min |
| 5 ul cells | N/A | N/A | 42.15 | 43.63 | 38.62 | 33.19 | ND | ND |
| 10 ul cells | N/A | N/A | 40.72 | 36.45 | 35.04 | 33.31 | 37.11 | 33.8 |
| 20 ul cells | N/A | N/A | 45.08 | 37.03 | 36.38 | 32.49 | ND | ND |

ND = not done.

As can be seen from Table 9 the preferred time and temperature for simultaneous lysis and conversion of human cells without pre-treatment lies between 90-95° C. for 15 minutes.

Figure 3:
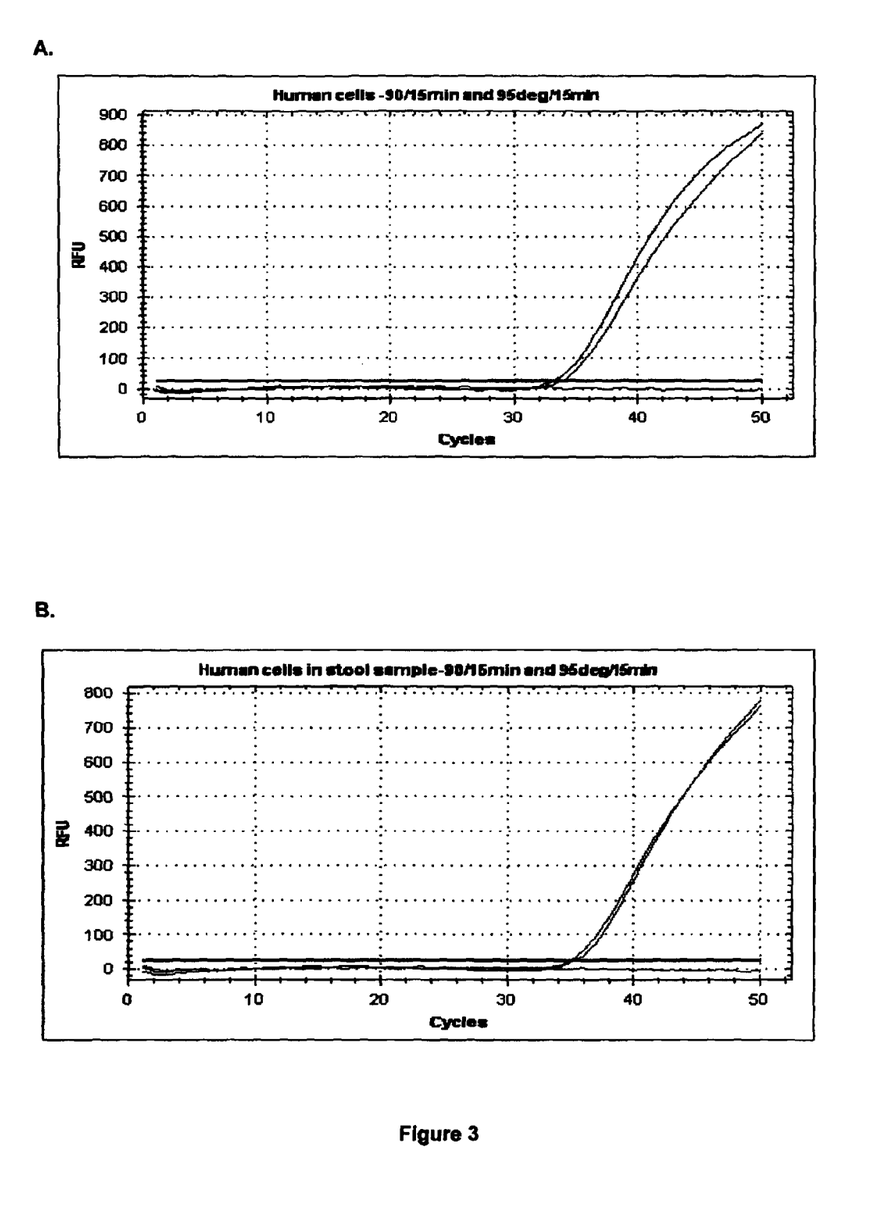

FIG. 3 shows the effect of spiking human cells into faecal material. FIG. 3A shows human MRC5 cells heated for 15 minutes in 3M bisulphite reagent at 95° C. then resuspended in high pH buffer (12.3) and amplified for the human β-globin gene. FIG. 3B shows the same cells spiked into faecal material heated for 15 minutes in 3M bisulphite reagent at 95° C. then resuspended in high pH buffer (12.3) and amplified for the human β-globin gene. As can be seen from the results human cells can be lysed and efficiently converted in primary human faecal material without any need for sample pre-processing or DNA isolation.

The results indicate that methylation profiling of human cells can be carried out directly on faecal samples obtained from patient without the need for pre-treatment or sample purification prior to bisulphite. Thus the method would be ideal as a non-invasive and simple method for the diagnosis of colorectal cancer directly from primary patient material.

Diagnostic Test Kits

The present invention can be provided in the form of diagnostic kits to allow the ease of use in a diagnostic laboratory or the like. Table 10 and Table 11 show the reagents provided in a typical test kit for a microorganism, for example. A kit includes instructions for use. It will be appreciated that tubes, swabs and other laboratory equipment may not be provided in a kit as those materials are usually readily available in a diagnostic laboratory.

TABLE 10

Box 1 of 2 (Store at room temperature)

| Component Name | Contents |
|---|---|
| Reagent 1 (Alkali water) | 5 × 5 mL |
| Reagent 2 (Bisulphite) | 5 × 3.5 g |
| Reagent 3 (Binding reagent) | 5 × 5.8 mL |
| Reagent 4 (Wash buffer) | 5 × 3 mL |
| Reagent 5 (Elution buffer) | 5 × 3 mL |
| Sheathed swabs | 100 |

TABLE 10-continued

Box 1 of 2 (Store at room temperature)

| Component Name | Contents |
|---|---|
| Reaction Tubes (1.5 mL) | 100 |
| Wash Tubes | 100 |
| Collection Tubes (1.5 mL) | 100 |

TABLE 10-continued

Box 1 of 2 (Store at room temperature)

| Component Name | Contents |
| --- | --- |
| Purification Columns | 100 |
| Detailed user guide | 1 |

TABLE 11

Box 2 of 2 (Store at -20° C. upon receipt)

| PCR mastermix | 5 × vials |
| --- | --- |
| PCR components | 5 × vials |

Box 2 should be stored at −20° C. in a DNA "clean room" in a different location to where the samples will be processed.

Kits for specific microorganisms or genetic tests include PCR primers to allow amplification of the target nucleic acid molecule.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A molecular detection assay comprising:
   treating a biological sample directly with a treating agent consisting of sodium bisulphite or sodium metabisulphite at a concentration of about 2.5M to 3.5M and a pH of about 4.5 to 5.5 and heating at a temperature of about 75° C. to 95° C. for about 1 to 30 minutes to allow cell disruption and nucleic acid treatment;
   removing the sodium bisulphite or sodium metabisulphite from the treated sample; and
   detecting a target nucleic acid in the treated sample,
   wherein the assay is carried out without pre-treatment of the biological sample prior to treating with the sodium bisulphite or sodium metabisulphite.

2. The assay according to claim 1 wherein the biological sample is selected from the group consisting of faecal, nasal, blood, plasma, serum, buccal cells, pus, wound, concentrated filtrates, cerebrospinal fluid, semen, liquid based cytology (LBC), tissue, FFPE, laser captured cells, cultured cells, pelleted cells, bacterial cultures, bacterial colonies, viral suspension, aspirate, bronchial lavage, sputum sample, environmental sample, environmental concentrate, foodstuff, raw ingredient, water sample and water concentrate.

3. The assay according to claim 1, wherein the assay is used to detect an infectious disease, a genetic disease or a genetic trait in an animal.

4. The assay according to claim 3, wherein the infectious disease is caused by a microorganism.

5. The assay according to claim 4, wherein the microorganism is a bacterium, virus, viroid, yeast, fungi, parasites, or amoeba.

6. The assay according to claim 2, wherein the genetic disease is cancer, a disease associated with copy number variation, an inherited disorder, an environmental induced disease, a disease caused by exposure to carcinogens, or a disease characterised by expansion or reduction in a nucleotide repeat length.

7. The assay according to claim 1, wherein the treating agent is used at a concentration of 3M at a pH of 5.0.

8. The assay according to claim 1, wherein the sample is heated for 10 to 20 minutes at a temperature of between 80° C. and 95° C.

9. The assay according to claim 1, wherein the sodium bisulphite or sodium metabisulphite is removed by column based purification, bead based purification or precipitation.

10. The assay according to claim 1, wherein after removal of the sodium bisulphite or sodium metabisulphite, the treated sample is resuspended in an elution buffer having a pH of at least 10.

11. The assay according to claim 10, wherein the elution buffer has a pH of 11.5 to 12.5.

12. The assay according to claim 11, wherein the elution buffer has pH of at least 12.

13. The assay according to claim 1, further comprising providing nucleic acid primers or probes to the treated sample.

14. The assay according to claim 13, wherein the target nucleic acid molecule is detected by amplification.

15. The assay according to claim 14, wherein the amplification is PCR, qPCR, reverse transcription PCR, digital PCR, isothermal amplification or signal amplification.

16. The assay according to claim 1, wherein the target nucleic acid is detected by sequencing the treated sample.

* * * * *

UNITED STATES PATENT AND TRADEMARK OFFICE
CERTIFICATE OF CORRECTION

PATENT NO. : 9,732,375 B2
APPLICATION NO. : 14/342093
DATED : August 15, 2017
INVENTOR(S) : Douglas Spencer Millar Page 1 of 2

It is certified that error appears in the above-identified patent and that said Letters Patent is hereby corrected as shown below:

Page 3, Column 1, Line 8, "Chern." should be --Chem.--.

Page 3, Column 1, Line 20, "tRNAH is" should be --tRNAHis--.

Page 3, Column 1, Line 36, "deoxyoxadenosine" should be --deoxyadenosine--.

Page 3, Column 1, Line 57, "Chern." should be --Chem.--.

Page 3, Column 1, Line 71, "Chern." should be --Chem.--.

Page 3, Column 2, Line 71, "Epigentic" should be --Epigenetic--.

Page 3, Column 2, Line 71, "sequencs" should be --sequences--.

Page 3, Column 2, Line 71, "Agricultureal" should be --Agricultural--.

Page 4, Column 1, Line 71, "Scuebces," should be --Sciences,--.

Page 4, Column 1, Line 53, "sensititive" should be --sensitive--.

Sheet 3 of 3, (Graph A., Figure 3), Line 1, "90/15min" should be --90deg/15min--.

Sheet 3 of 3, (Graph B., Figure 3), Line 1, "90/16min" should be --90deg/15min--.

Column 4, Line 2, after "virus" insert --.--.

Column 4, Line 6, "R-globin" should be --β-globin--.

Column 4, Line 10 (approx.), "R-globin" should be --β-globin--.

Signed and Sealed this
Ninth Day of January, 2018

Joseph Matal
*Performing the Functions and Duties of the
Under Secretary of Commerce for Intellectual Property and
Director of the United States Patent and Trademark Office*

Column 4, Line 60, "Camplylobacter" should be --Campylobacter--.

Column 12, Line 2, "(Zeptoometrix)" should be --(Zeptometrix)--.

Column 12, Line 47 (approx.), "virus" should be --virus).--.

Column 12, Line 49 (approx.), after "virus)" insert --.--.